United States Patent
Schroeder et al.

(10) Patent No.: US 10,130,745 B2
(45) Date of Patent: *Nov. 20, 2018

(54) PACKAGING OF POWDERY MATERIAL FOR PREPARATION OF A MEDICAL SOLUTION

(71) Applicant: GAMBRO LUNDIA AB, Lund (SE)

(72) Inventors: Petronella Schroeder, Stockholm (SE); Olof Jansson, Vellinge (SE); Torbjorn Linden, Hasslo (SE)

(73) Assignee: GAMBRO LUNDIA AB, Lund (SE)

( * ) Notice: Subject to any disclaimer, the term of this patent is extended or adjusted under 35 U.S.C. 154(b) by 0 days.

This patent is subject to a terminal disclaimer.

(21) Appl. No.: 15/705,872

(22) Filed: Sep. 15, 2017

(65) Prior Publication Data
US 2018/0008761 A1    Jan. 11, 2018

Related U.S. Application Data

(63) Continuation of application No. 14/898,182, filed as application No. PCT/EP2014/062112 on Jun. 11, 2014, now Pat. No. 9,782,530.

(30) Foreign Application Priority Data

Jul. 5, 2013 (SE) ........................ 1350845

(51) Int. Cl.
  *A61M 1/16* (2006.01)
  *A61J 1/10* (2006.01)
  (Continued)

(52) U.S. Cl.
  CPC .............. *A61M 1/1666* (2014.02); *A61J 1/10* (2013.01); *A61J 1/2093* (2013.01); *A61M 1/167* (2014.02);
  (Continued)

(58) Field of Classification Search
  CPC ..... A61B 19/00; A61J 1/10; A61J 1/20; A61J 1/2093; A61M 1/16; A61M 1/1666;
  (Continued)

(56) References Cited

U.S. PATENT DOCUMENTS 2,597,715 A    5/1952   Eriksson et al.
2,803,115 A    8/1957   Shepherd
(Continued)

FOREIGN PATENT DOCUMENTS

CN    1097599    1/1995
CN    102770167    11/2012
(Continued)

OTHER PUBLICATIONS

Office Action issued in related Chinese patent application No. 201480001377, dated Jan. 26, 2016. 11 pages.
(Continued)

*Primary Examiner* — Bryon Gehman
(74) *Attorney, Agent, or Firm* — K&L Gates LLP

(57) ABSTRACT

A package (1) is configured to store a powdery material (2) which is to be mixed with a solvent to form a medical solution, such as a dialysis solution. The package (1) comprises a filled cavity portion (6a) containing the powdery material (2), optionally separated into groups of different composition, and a tab portion (9) integrally formed with the filled cavity portion (6a) and being swept around the filled cavity portion (6a) so as to define a roll-up package. The tab portion (9) forms a protective barrier that shields the powdery material (2), e.g. by counteracting transport of moisture into and out of the package. The tab portion (9) may also stabilize the package. The roll-up package is compact, and simple to manufacture and handle.

20 Claims, 4 Drawing Sheets

(51) Int. Cl.
*A61J 1/20* (2006.01)
*B65B 3/00* (2006.01)
*B65B 7/02* (2006.01)
*A61M 1/28* (2006.01)

(52) U.S. Cl.
CPC ............. *A61M 1/287* (2013.01); *B65B 3/003* (2013.01); *B65B 7/02* (2013.01); *A61M 2207/00* (2013.01)

(58) Field of Classification Search
CPC ........ A61M 1/167; A61M 1/28; A61M 1/287; A61M 2207/00; B65B 3/003; B65B 7/02; B65B 3/00; B65D 35/00; B65D 35/34; B65D 65/02; B65D 65/14; B65D 81/3266; B65D 81/32
USPC .... 206/219, 221, 438, 568, 570–572; 222/1, 222/92–107, 183
See application file for complete search history.

(56) References Cited

U.S. PATENT DOCUMENTS

| | | | |
|---|---|---|---|
| 3,079,919 | A | 3/1963 | Harrison et al. |
| 3,575,755 | A | 4/1971 | Cutler et al. |
| 4,402,402 | A | 9/1983 | Pike |
| 4,573,954 | A | 3/1986 | Berger et al. |
| 4,731,053 | A | 3/1988 | Hoffman |
| 4,793,123 | A | 12/1988 | Pharo |
| 4,997,083 | A | 3/1991 | Loretti et al. |
| 5,610,170 | A | 3/1997 | Inoue et al. |
| 6,308,827 | B1 | 10/2001 | Hacikyan |
| 6,834,480 | B1 | 12/2004 | Ishino et al. |
| 7,875,016 | B2 | 1/2011 | Pahlberg et al. |
| 8,118,158 | B2 | 2/2012 | Igota et al. |
| 8,343,129 | B2 | 1/2013 | Falkvall et al. |
| 8,550,301 | B2 | 10/2013 | Szymanski |
| 9,138,380 | B2 | 9/2015 | Jansson et al. |
| 9,320,680 | B2 | 4/2016 | Schroeder |
| 2003/0052033 | A1 | 3/2003 | Schwester |
| 2004/0112785 | A1 | 6/2004 | Wittmeier |
| 2009/0090643 | A1 | 4/2009 | Fischer et al. |
| 2009/0260739 | A1 | 10/2009 | Fischer et al. |
| 2010/0219094 | A1 | 9/2010 | Moteki et al. |
| 2012/0310150 | A1 | 12/2012 | Brandl et al. |
| 2013/0008825 | A1 | 1/2013 | McArthur et al. |

FOREIGN PATENT DOCUMENTS

| | | |
|---|---|---|
| EP | 0042336 | 12/1981 |
| FR | 2835511 | 8/2008 |
| GB | 2436323 | 9/2007 |
| JP | H03275456 | 12/1991 |
| JP | H10203505 | 8/1998 |
| JP | 2004268925 | 9/2004 |
| JP | 2007069950 | 3/2007 |
| WO | 8200441 | 2/1982 |
| WO | 83/03587 | 10/1983 |
| WO | 9312003 | 6/1993 |
| WO | 9906083 | 2/1999 |
| WO | 2007076239 | 7/2007 |
| WO | 2007144427 | 12/2007 |
| WO | 2011161064 | 12/2011 |

OTHER PUBLICATIONS

Search Report for related Chinese patent application No. 201480001377, dated Jan. 17, 2016. 3 pages.
International Search Report; PCT/EP2014/064744; dated Sep. 16, 2014; 6 pages.
Written Opinion; PCT/EP2014/064744; dated Sep. 16, 2014; 8 pages.

PACKAGING OF POWDERY MATERIAL FOR PREPARATION OF A MEDICAL SOLUTION

PRIORITY CLAIM

The present application claims priority to and the benefit as a continuation application of U.S. patent application Ser. No. 14/898,182, entitled "Packaging of Powdery Material For Preparation of A Medical Solution", filed Dec. 14, 2015, which is a National Stage of International Application No. PCT/EP2014/062112, filed Jun. 11, 2014, which in turn claims priority to Swedish Patent Application No. 1350845-2, filed Jul. 5, 2013, the entire contents of each of which are incorporated herein by reference and relied upon.

TECHNICAL FIELD

The present disclosure relates to a package for storing powdery material which is to be mixed with a solvent to form a medical solution.

BACKGROUND

One type of treatment for patients having substantially impaired renal function, or kidney failure, is known as "dialysis". Either blood dialysis ("hemodialysis") or peritoneal dialysis ("PD") methods may be employed. Both methods essentially involve the removal of toxins from body fluids and restoration of such body fluids by diffusion and/or convection by means of a dialysis solution.

Patients receiving hemodialysis typically utilize 75 to 200 liters of prepared dialysis solution three times a week. The largest ingredient in these solutions is water.

Conventionally, dialysis solutions for hemodialysis are prepared from separate concentrated solutions. For example, one concentrate, Preparation A, includes a mixture of varied salts, sugars and acids dissolved in water. Another concentrate, Preparation B, is made of sodium bicarbonate dissolved in water, and may also contain sodium chloride. The constituents must be kept separate until shortly before hemodialysis because of the tendency for insoluble precipitates to form in the combined solution.

Even in concentrated solutions, the Preparations A and B are themselves bulky and difficult to transport. Moreover, bicarbonate solutions such as Preparation B have a tendency to form carbon dioxide and alter the pH of their solution over extended periods of time, even if not mixed with other components. Another logistical problem with preparing dialysis solutions is the need to keep the solutions essentially free of bacteria and endotoxins.

In PD, the patient's peritoneal cavity is filled with a dialysis solution. The dialysis solution is generally formulated with a high concentration of the dextrose, as compared to body fluids, resulting in an osmotic gradient within the peritoneal cavity. The effect of this gradient is to cause body fluids, including impurities, to pass through the peritoneal membrane and mix with the dialysis solution. By draining the spent dialysis solution from the cavity, the impurities are removed.

In PD, the dialysis solution is administered directly into the patient's body, and it is thus important that the dialysis solution is sterile and maintains the correct proportions and concentrations of components. Conventionally, for PD, dialysis solutions are delivered to the site of administration in pre-mixed solutions.

Similar to dialysis solutions for hemodialysis, the dialysis solutions used in PD are not stable over time due to incompatibility of the components in these solutions. For example, dextrose has a tendency to caramelize in solution over time, and bicarbonate ions react undesirably with calcium and magnesium in solutions to form insoluble calcium carbonate or magnesium carbonate. Bicarbonate can also spontaneously decompose into carbon dioxide and water.

Significant research efforts have been spent on providing dry formulations of components that are subsequently mixed with a solvent, typically water, to form dialysis concentrates or dialysis solutions. The use of dry formulations in the form of powdery material has the potential of increasing shelf life, reduce the formation of possible degradation products, and reduce the weight and volume of the material that needs to be transported to and stored at the dialysis treatment sites.

However, there are difficulties in using dry formulations for preparation of dialysis concentrates and dialysis solutions.

One difficulty associated with the use of dry formulations is that certain components of the dry formulations are incompatible and therefore have to be stored separately. Some of the components, e.g. magnesium chloride, calcium chloride and glucose, typically bind water molecules, at least in their commonly used forms, while other components, e.g. NaCl, are hygroscopic. If the former component(s) releases water during storage, the latter component(s) may form lumps or cakes, and these lumps/cakes may be difficult to dissolve when preparing the dialysis solution. If bicarbonates and acids are mixed, gases may be formed in the presence of water. If glucose and acids are mixed and subject to non-dry conditions, the glucose may be degraded and discolored. These problems may be overcome by storing the different dry formulations in separate packages. Another way of dealing with these problems is to separate the dry formulations into compatible groupings, which are arranged to be physically separated within the package. Such packages are e.g. known from US2006/0115395, WO2007/144427 and WO2011/161064, and are designed to reduce the risk for incorrect composition of the dialysis solution due to incorrect handling.

It may also be important to design the package so as to prevent moisture from entering or leaving the package during storage and transport, for example to avoid that water enters the package from the outside to degrade the dry formulation or causing it to release gases, or to avoid that bound water is released from the dry formulation and leaves the package. To achieve an effective barrier against moisture transport, the wall thickness of the package may be increased or the package may be manufactured in a dedicated vapor barrier material. It is also possible to protect the package by a dedicated overwrap, e.g. a separate plastic film which is arranged around the package and attached by adhesive, tape or heat sealing, e.g. by so-called shrink wrapping. All of these solutions increase the cost for the package.

There are other design criteria for the package that may or may not be important, e.g. to make the package compact and easy to store, to make the package easy to handle when the dialysis solution is to be prepared, to make the package easy to manufacture, etc.

Although the foregoing discussion is given in relation to preparation of dialysis solutions, it is to be understood that corresponding problems and needs are equally and generally valid for the preparation of other types of medical solutions, such as replacement solutions, infusion solutions or nutritional solutions.

SUMMARY

It is an objective of the disclosure to at least partly overcome one or more of the above-identified limitations of the prior art.

One objective is to provide an alternative package for storing powdery material which is to be mixed with a solvent to form a medical solution.

Another objective is to provide such a package with a design that limits moisture transport into and out of the package.

Yet another objective is to provide such a package which is simple to use when preparing the medical solution.

A further objective is to provide such a package which is compact during storage.

A still further objective is to provide such a package which is simple to manufacture.

Another objective is to provide such a package that enables separated storage of plural sets of powdery material within the package.

One or more of these objectives, as well as further objectives that may appear from the description below, are at least partly achieved by means of a package, a use and a method of manufacturing according to the independent claims, embodiments thereof being defined by the dependent claims.

A first aspect of the disclosure is a package for storing powdery material which is to be mixed with a solvent to form a medical solution, the package comprising: a filled cavity portion containing the powdery material, and a tab portion integrally formed with the filled cavity portion and being swept around the filled cavity portion so as to form a roll-up package.

By way of the tab portion that is swept around the filled cavity portion, the powdery material in the package is inherently better shielded from the surroundings than in a conventional package without such a tab portion. The tab portion will form a protective barrier that counteracts transport of moisture into and out of the package. This may be used to provide a package with good resistance to moisture transport even if the package is made of a cheaper material with less vapor resistance. By the same token, it is possible to reduce the material thickness in the package.

The package is formed as a roll-up package and is thereby compact during storage and transport. The tab portion may also contribute to improve the general durability and stability of the package during storage and transport.

The provision of the tab portion may make it possible to dispense with the conventional overwrap, thereby simplifying manufacture by removing the need for a separate processing step and costly machinery for producing the overwrap. However, it should be noted that an overwrap may be used with the inventive package, e.g. to ensure a sterile environment around the package, to protect the package from contamination such as dust, or to provide a further vapor barrier.

The package is simple to handle when the medical solution is to be prepared. A user may simply prepare the package for use by unwinding or unfolding the tab portion from the filled cavity portion.

It should be noted that the "filled cavity portion" need not be completely filled with the powdery material. Part of the filled cavity portion may be void of powdery material, and this part may be either evacuated or contain a gas, e.g. air. Thus, the filled cavity portion is filled in the sense that it contains the powdery material.

The roll-up package is thus a package in the form of a roll of package material around a core of powdery material. Typically, such a roll-up package is generally cylindrical, and the tab portion may be swept in at least one full turn, and preferably at least two full turns, around the filled cavity portion.

In one embodiment, the package defines a sealed cavity that includes the filled cavity portion and an empty cavity portion which is free of powdery material and is located adjacent to the filled cavity portion, wherein the tab portion includes the empty cavity portion. This embodiment makes it possible to admit the solvent into the sealed cavity when preparing the medical solution, e.g. via a connector on the package, for mixing with the powdery material inside the package. The empty cavity portion is free of powdery material and offers room for mixing within the sealed cavity when the package is unfolded. At the same time, the empty cavity portion contributes to the protective function of the tab portion when the tab portion is swept around the powdery material during storage and transport. This will reduce the required amount of material in the package. Furthermore, if the empty cavity portion is defined between two overlapping sheets which are swept around the powdery material, the protective function of the tab portion will be improved.

In one embodiment, the package is defined by first and second overlapping sheets of flexible material which are joined to define the sealed cavity. This embodiment is simple to manufacture and may utilize a minimum of package material. The resulting roll-up package is compact. Further, as noted above, an improved protective function is achieved since the tab portion is at least partly defined by overlapping sheets that are swept around the powdery material.

In one embodiment, the sealed cavity extends from a first cavity end to a second cavity end, the powdery material being arranged in the sealed cavity such that the filled cavity portion is located at the first cavity end and the empty cavity portion extends from the filled cavity portion towards the second cavity end. This embodiment will maximize the amount of material that is swept around the powdery material for a given extent between first and second cavity ends.

The overlapping sheets may be made of plastic material, and the sheet may be joined by a circumferential weld line to define the sealed cavity between the sheets.

Non-limiting examples of materials for the overlapping sheets include polyolefin materials such as polypropylene (PP), polyethylene (PE), polyamide (PA), cyclic olefin copolymer (COC), polystyrene (PS), styrene-ethylene-butylene-styrene triblock copolymers (SEBS), styrene-ethylene-propylene-styrene triblock copolymers (SEPS), and polychlorotrifluoroethylene (PCTFE), homogeneous or laminated in any combination, with a total thickness of about 0.1-0.5 mm, preferably about 0.25-0.3 mm. The material may further have a water vapor transmission rate less than 0.3 g/m$^2$/day at 38° C./90% RH, or even less than 0.2 g/m$^2$/d at 38° C./90% RH.

In one embodiment, the filled cavity portion and the empty cavity portion are separated by a releasable seal that joins the first and second overlapping sheets. The releasable seal is thus a divider that may be opened or ruptured during the mixing process to establish communication between the filled cavity portion and the empty cavity portion. This embodiment ensures that the powdery material stays in the filled cavity portion during storage and transport, while at the same time allowing the powdery material to be mixed with the solvent in the sealed cavity when the package has been unfolded. The package may be designed to automatically rupture the releasable seal when the package is unfolded, or the releasable seal may be designed to rupture by forces exerted by the solvent when admitted into the package. Alternatively, the user may manually tear the sheets apart to rupture the releasable seal.

In an alternative embodiment, the filled cavity portion and the empty cavity portion are separated by a constriction region, in which the first and second overlapping sheets are brought into close proximity with each other without being fixedly attached to each other, by action of a force generated by the tab portion being swept around the filled cavity portion. This embodiment ensures that the powdery material stays in the filled cavity portion during storage and transport. Further, communication between the filled cavity portion and the empty cavity portion is automatically established when the package is unfolded, since the force holding the sheets together in the constriction region is relaxed when the tab portion is unwound. Compared to using a releasable seal, the use of a constriction region may simplify manufacture of the package.

In one embodiment, the filled cavity portion comprises two sub-cavities that are located side by side from the first cavity end towards the second cavity end and are separated from each other at a fold line in the first and second overlapping sheets, the two sub-cavities containing a respective set of powdery material, wherein the two sub-cavities are folded onto each other along the fold by action of a force generated by the tab portion being swept around the filled cavity portion. This embodiment enables a compact package even if the package contains more than one set of powdery material. The sets of powdery material are separated from each other in the roll-up package, at the fold line, e.g. to prevent or at least impede undesired mixing of powdery material between the sets and/or migration of water from one set to another. The sets may be separated from each other by a constriction region that is formed by the fold line. Alternatively, a releasable seal may be arranged at the fold line. The package may include more than two sub-cavities that contain a respective set of powdery material. Thus, the package may define a chain of sub-cavities from the first cavity end, which are separated in pairs at a respective fold line and which are folded onto each other in the roll-up package.

In an alternative embodiment, the filled cavity portion comprises an elongated internal partition which joins the first and second overlapping sheets and is arranged to extend in a direction from the first cavity end towards the second cavity end, wherein a respective set of powdery material is arranged in each of two pockets which are defined between the first and second overlapping sheets and are separated by the elongated internal partition. In this embodiment, the internal partition is permanent (non-releasable). If the package is formed by two overlapping sheets of plastic material, the partition may be formed by a weld line through the overlapping sheets. The internal partition is arranged to locate the pockets, and thus the sets of powdery material, side by side along the first cavity end. This may reduce the size of the roll-up package and may also serve to reduce the tension in the sheet material of the roll-up package. The provision of pockets may hinder undesired mixing of powdery material between the sets and/or migration of water from one set to another. The package may include more than one elongated internal partition that extends in a direction from the first cavity end towards the second cavity end, so as to define more than two separated pockets along the first cavity end in the package.

In an alternative embodiment, the filled cavity portion comprises an elongated internal partition which joins the first and second overlapping sheets and is arranged with a spacing from the first cavity end such that an open pocket is defined between the elongated internal partition and the first cavity end in the filled cavity portion, wherein at least part of the powdery material is arranged in the open pocket. The open pocket is thus open with respect to the filled cavity portion and may serve to immobilize the powdery material within the filled cavity portion during manufacture, e.g. when the tab portion is swept around the filled cavity portion. The open pocket allows the powdery material to mix with a solvent which is admitted into the sealed cavity when the package has been unfolded. The internal partition is permanent (non-releasable) and may, but need not, coincide with the border between the empty cavity portion and the filled cavity portion. The package may include two or more elongated internal partitions that are located at different distances from the first cavity end, so as to define two or more separated open pockets within the filled cavity portion. The pockets may thereby be arranged side by side from the first cavity end towards the second cavity end. Each pocket may contain a respective set of powdery material. The internal partitions may define fold lines, and the pockets may be folded onto each other along the fold lines in the roll-up package.

In one embodiment, the sealed cavity is evacuated to a sub-atmospheric pressure. This ensures that the package is compact. By evacuating gases from the sealed cavity it may be easier to sweep the tab portion around the powdery material during manufacture. The evacuation may also immobilize the powdery material in the sealed cavity, which may be advantageous during manufacture as well as during storage and transport.

In one embodiment, the package further comprises a connector attached to a wall portion of the empty cavity portion for admitting a fluid and enabling mixing of the powdery material with a solvent within the sealed cavity as part of a process for preparing the medical solution. In an alternative embodiment, the package has no integrated connector, but instead a separate connector is provided for attachment to the wall portion of the package when the package has been unfolded in preparation of mixing. In yet another variant, the connector is attached to a wall portion of the filled cavity portion.

In one embodiment, the filled cavity portion contains at least two separated sets of powdery material of different compositions. If the sets of powdery material have different hygroscopic properties and are located in the filled cavity portion side by side from the first cavity end towards the second cavity end, it is preferable that the set of powdery material that is most hygroscopic is located at the first cavity end. Thereby, powdery material that is most sensitive to moisture is located at the core of the roll-up package so as to be most shielded from moisture in the surroundings of the package.

In one embodiment, the package further comprises a suspension hole in the tab portion. This embodiment facilitates handling of the package when the medical solution is to be prepared, since the weight of the powdery material will assist the unfolding of the package when the package is suspended at the tab portion.

In one embodiment, the medical solution is one of a dialysis concentrate, a dialysis solution, an infusion solution, a nutrition solution, a replacement solution, and a plasma expander solution.

In one embodiment, the powdery material comprises an acid concentrate powder for preparation of an acid concentrate for use in dialysis.

A second aspect of the disclosure is a use of the package according to the first aspect in blood dialysis treatment or in peritoneal dialysis treatment.

A third aspect of the disclosure is a method of manufacturing a package for storing powdery material which is to be mixed with a solvent to form a medical solution, said method comprising: providing a package blank that defines an interior space between two overlapping sheets of flexible material, disposing the powdery material in the interior space at a first end of the interior space while leaving a non-filled portion that extends from the powdery material to an opposite end of the interior space, sealing the interior cavity of the package blank to form a sealed cavity comprising the non-filled portion and a filled cavity portion containing the powdery material, and sweeping a portion of the package blank, including the non-filled portion of the sealed cavity, around the filled cavity portion, so as to define a roll-up package.

The "package blank" generally refers to any intermediate product which is supplied to a filling station which dispenses the powdery material into the interior space. The package blank may be manufactured upstream of the filling station in a production line that contains the filling station, or it may be manufactured in a separate production line and delivered to the filling station.

The third aspect may be implemented with manufacturing steps to provide the package with any of the structural features that are described above in relation to embodiments of the first aspect.

Still other objectives, features, aspects and advantages of the present disclosure will appear from the following detailed description, from the attached claims as well as from the drawings.

BRIEF DESCRIPTION OF THE DRAWINGS

Embodiments of the disclosure will now be described in more detail with reference to the accompanying schematic drawings.

DETAILED DESCRIPTION

Figure 1A:
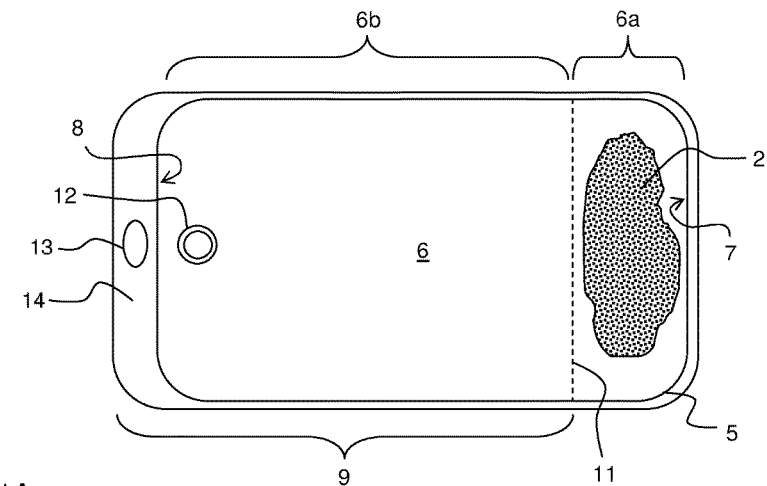
FIGS. 1A-1B are top plan and section views of an unfolded package according to a first embodiment.

The present disclosure relates to packages that store one or more powders for subsequent use in preparation of a medical solution, e.g. a dialysis solution. Although the technical effects are achieved by the finished package in a transport/storage stage, embodiments of the package will also be illustrated and described in an unfolded state. Even if all structural elements of the package are not visible or indicated when the package is shown in the transport/storage state, they are intended to be inferred from the illustrations of the package in the unfolded state.

Throughout the description, the same reference numerals are used to identify corresponding elements.

Figure 1B:
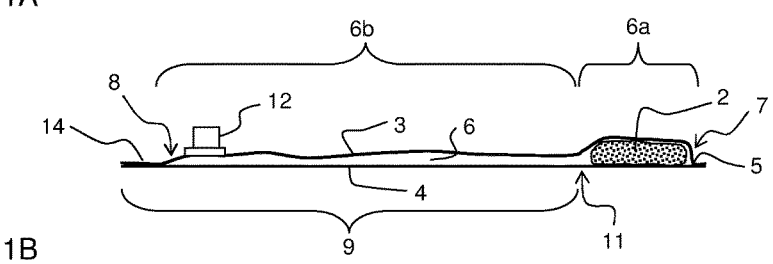
Figure 1C:
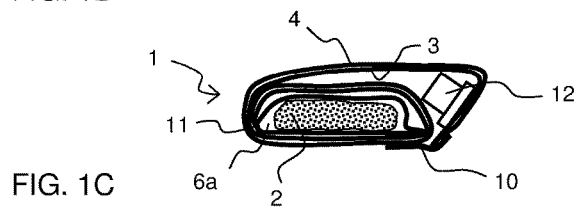
FIG. 1C is a side view of a roll-up package formed by the package in FIGS. 1A-1B.

FIGS. 1A-1C illustrate a first embodiment of a package or bag 1 that contains a powdery material 2 (abbreviated "powder" in the following) for use in preparation of a dialysis solution or a concentrate to be further diluted to a ready for use dialysis solution, hereafter collectively referred to as a dialysis solution. FIG. 1C is a side view of the finished package 1, which has the form of generally cylindrical roll with the powder 2 located at the center of the roll. This type of package is generally denoted a "roll-up package" herein. FIGS. 1A-1B show the package in an unfolded or flat state. Two overlapping, flexible sheets 3, 4 of plastic material are joined by a permanent seal 5, e.g. a weld line, to form an interior cavity 6. The sheets 3, 4 may also be joined outside of the seal 5 to form a circumferential frame portion, e.g. by heat fusing, gluing, etc. The interior cavity 6 has the dual function of being a storage compartment for holding the powder 2 and a mixing compartment for mixing the powder with a solvent, e.g. water, for preparation of the dialysis solution. In the flat state, the interior cavity 6 is generally rectangular in plan view (FIG. 1A) and extends between the sheets 3, 4 from a first cavity end 7 to a second cavity end 8. The powder 2 is located between the sheets 3, 4 at the first cavity end 7, in a first cavity portion 6a denoted "powder portion" in the following. The rest of the cavity 6 is free of powder and is denoted "empty portion" in the following, designated by reference numeral 6b. The overlapping sheets 3, 4 form a tab or flap 9 which extends from the powder portion 6a. The empty portion 6b forms part of the tab 9. As seen in FIG. 1C, the tab 9 is wound or swept around the powder portion 6a to form the roll-up package 1. A piece of adhesive tape 10 is applied to attach the free end of the tab 9 onto the roll-up package 1. The tape 10 is preferably designed to be tamper indicating, e.g. by forcing the user to break the tape to detach and unwind the tab 9 from the package 1. In the roll-up package 1, the cavity 6 is physically separated into the powder portion 6a and the empty portion 6b. The border 11 between the cavity portions 6a, 6b is indicated by a dashed line in FIG. 1A. This border extends in the axial direction of the roll-up package 1, which generally has the shape of a cylinder (cf. FIG. 1D). As seen in the side view of FIG. 1B, there is no physical barrier at the border 11 between the cavity portions 6a, 6b in the flat state, i.e. the sheets 3, 4 are not fixedly connected at the border 11. However, when the tab 9 is wound around the powder portion 6a, the opposing sheets 3, 4 are pressed against each other to form a constriction region at the border 11, as shown in FIG. 1C. In this constriction region, the opposing sheets 3, 4 are brought into close proximity or abutment with each other such that migration of the powder 2 into the empty portion 6b is prevented or at least significantly obstructed. It is conceivable that a deformation is formed one or both sheets 3, 4 to promote formation of the constriction region. To further immobilize the powder 2, the cavity 6 may be evacuated to a sub-atmospheric pressure.

The package 1 further includes a connector 12 which is in fluid communication with the cavity 6. The connector 12, which may be sealed in the transport/storage state, is adapted for connection to a supply of a solvent, e.g. water. In the illustrated embodiment, the connector 12 is attached to the sheet 3 which is wrapped onto the powder sub-cavity 6a, such that connector 12 is shielded inside the roll-up package 1.

A suspension hole 13 is formed in the frame portion 14 that extends from the cavity end 8 to the distal end of the tab 9. The suspension hole 13 may be used for hanging the package from a hook or the like when the package is used for preparing the dialysis solution. By arranging the suspension hole 13 in the frame portion 14, the unfolding of the package will be assisted by the weight of the powder 2. In a variant (not shown), the suspension hole 13 is formed in a material portion adjacent to the first cavity end 7. Thereby, gravity will drive the powder 2 into the empty portion 6b when the package is suspended, which may help to dissolve the powdery material and reduce the impact of potential caking and lumping of the powdery material.

The package 1 is delivered to the dialysis site in the transport/storage state shown in FIG. 1C. When the dialysis solution is to be prepared, the seal formed by the tape 10 is broken and the tab 9 is unwound from the package. When the tab 9 is unwound, the forces acting on the border 11 are relaxed and communication between the portions 6a, 6b is established or at least enabled. At this time, the unwound package may be suspended at the hole 13. The connector 12 is then coupled to a supply for a solvent, in this example a water supply. The water supply is operated to introduce a carefully metered volume of water into the cavity 6, whereby the cavity 6 is expanded and the powdery material is dissolved in the water to form the dialysis solution. Thus, the cavity 6 is used as a mixing chamber for the preparation of the dialysis solution. Finally, the dialysis solution is extracted from the cavity 6 through the connector 12.

It should be noted that the roll-up package 1 may be provided without an integrated connector 12. In such a variant, a separate connector may be attached to the package as part of the process of preparing the dialysis solution, e.g. when the tab 9 has been unwound and the package is in a flat state.

Figure 1D:
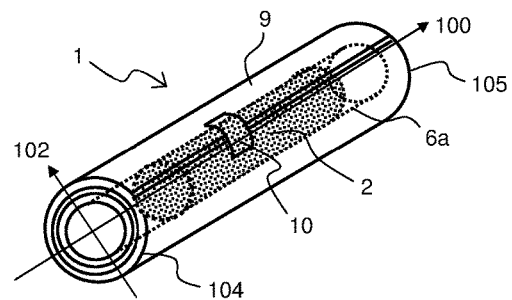
FIG. 1D is a generalized perspective view of the roll-up package in FIG. 1C.

FIG. 1D is a generalized perspective view of a roll-up package 1 according to the first embodiment, in a variant without a connector. As seen, the roll-up package 1 has the general shape of a cylinder with an axial direction 100 and a radial direction 102. The package 1 extends between two axial ends 104, 105. The tab 9 is swept a number of turns around the powder portion 6a, which forms the core of the cylinder. In the radial direction 102, the powder 2 is thus not only enclosed by the walls of the powder portion 6a, but also by the material of the tab 9. Thereby, the tab 9 forms an additional barrier that both improves the durability and stability of the package 1 and shields the powder 2 from the surroundings, e.g. with respect to moisture transport, dust, sunlight, oxidation, etc. Further, the roll-up package 1 of the first embodiment permits economization of raw material since the empty portion 6b, which is designed to receive the solvent during the mixing process, is located in the tab 9 and thus has the additional function of protecting the powder 2 during transport and storage. Further, since the cavity 6 is defined between overlapping sheets 3, 4, the powder 2 will be protected by two additional layers of material for each full turn of the empty portion 6b around the powder portion 6a. Still further, a simple yet still effective separation of the portions 6a, 6b is achieved if the tab 9 is tightly drawn around the powder portion 6b such that the sheets 3, 4 are pressed together at the border 11.

Figure 1E:
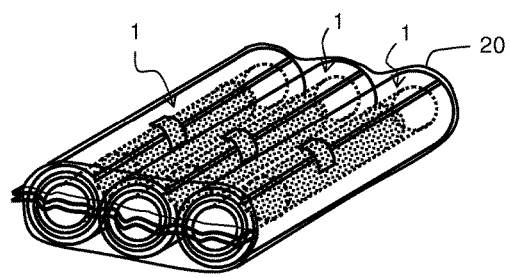
FIG. 1E is a perspective view of a set of packages in an overwrap.

The roll-up package 1 may be stored and transported in the configuration shown in FIG. 1D. For example, a plurality of roll-up packages 1 may be stacked in a cardboard box for shipping. However, it is also conceivable that each roll-up package 1, or a plurality of roll-up packages 1, are placed in an overwrap of plastic material or paper, as is well-known in the art. FIG. 1E is a perspective view of three roll-up packages 1 which are contained in and held together by such an overwrap 20. The overwrap 20 may be used to keep the roll-up packages 1 clean, and possibly sterile, during transport and storage. The roll-up packages 1 in each overwrap 20 may be identical or they may contain different powdery material for preparation of different dialysis solutions, e.g. for use during a dialysis treatment. The overwrap 20 may also be configured to provide additional protection against moisture transport into and out of the package, e.g. via the axial ends 104, 105 (FIG. 1D). If each overwrap 20 contains a single package, the overwrap 20 may be designed to replace or supplement the tape 10 as a means for affixing the tab 9 and stabilizing the roll-up package 1. This may be achieved by a shrink wrap.

Figure 1F:
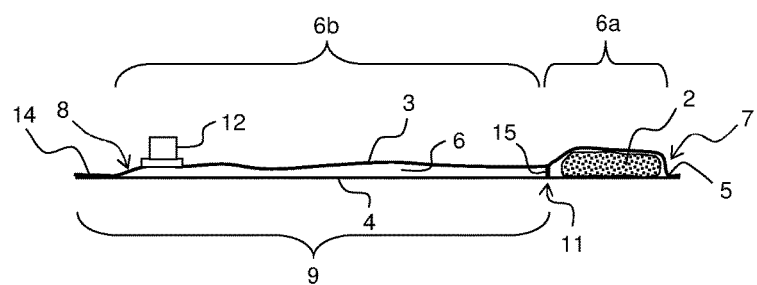
FIG. 1F is a side view of a variant of the unfolded package in FIG. 1B.

FIG. 1F is a side view of a variant of the first embodiment and corresponds to FIG. 1B. The foregoing description is equally applicable to this variant, which differs from the first embodiment only in that a releasable seal 15 is installed at the border 11 between the cavity portions 6a, 6b. The releasable seal 15 extends across the entire width of the package in the axial direction (along the dashed line 11 in FIG. 1A) and forms a physical barrier between the portions 6a, 6b in the roll-up package 1. The releasable seal 15 is thus a divider which is arranged to join the opposing sheets 3, 4 at the border 11 and which is ruptured as part of the process for preparing the dialysis solution. Releasable seals as such are known to the skilled person.

Figure 2A:
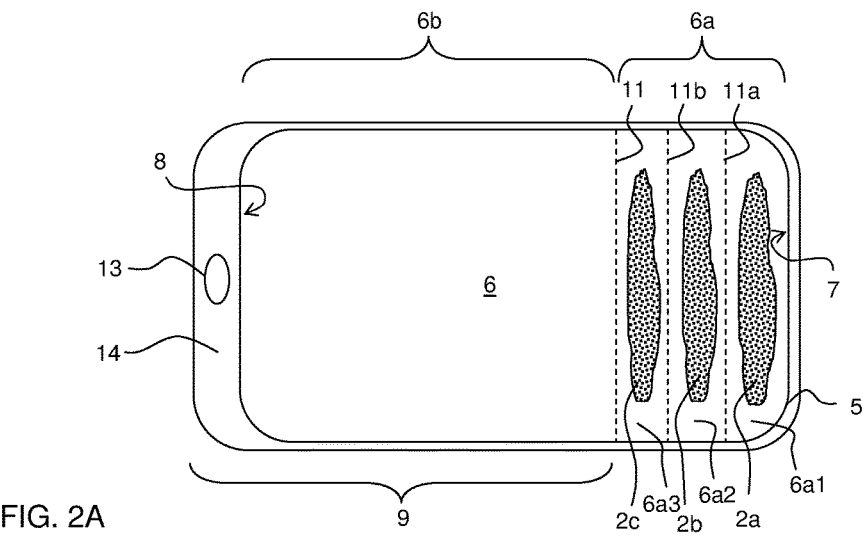
FIG. 2A is a top plan view of an unfolded package according to a second embodiment.
Figure 2B:
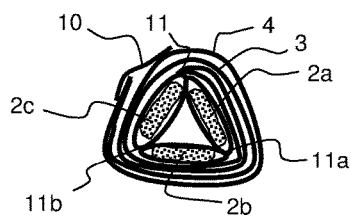
FIG. 2B is a side view of a roll-up package formed by the package in FIG. 2A.

FIGS. 2A-2B illustrate a second embodiment, in which the powdery material is separated into three powder groups 2a, 2b, 2c of different compositions. Each powder group 2a, 2b, 2c contains either a single dry substance or a combination of compatible dry substances. In this context a "dry substance" denotes a substance in solid form. It should be noted that a dry substance may still contain water, e.g. if the water molecules are incorporated in a crystal lattice, so-called water of crystallization. Each powder group 2a, 2b, 2c is located in a respective sub-cavity or pocket 6a1, 6a2, 6a3 in the powder portion 6a. The sub-cavities 6a1, 6a2, 6a3 are separated by a respective fold line 11a, 11b. The sub-cavities 6a1, 6a2, 6a3 are thereby arranged side by side in the powder portion 6a to extend in the axial direction of the roll-up package 1. The sub-cavities 6a1, 6a2, 6a3 are folded one onto the other along the respective fold line 11a, 11b, starting from the innermost sub-cavity 6a1, as shown in the side view of FIG. 2B. The fold lines 11a, 11b form a respective constriction region for separation of the powder groups. The border 11 between the powder portion 6a and the empty portion 6b may be defined as in the first embodiment or any of its variants. If the powder groups 2a, 2b, 2c have different hygroscopic properties, it may be desirable to locate the most hygroscopic material in the innermost sub-cavity 6a1, which is most shielded from moisture in the surroundings of the roll-up package 1.

In a variant of the second embodiment, one or more of the sub-cavities 6*a*1, 6*a*2, 6*a*3 are separated by a respective releasable seal. In such a variant, the sub-cavities 6*a*1, 6*a*2, 6*a*3 need not, but may, be folded onto each other as shown in FIG. 2B.

Figure 3:
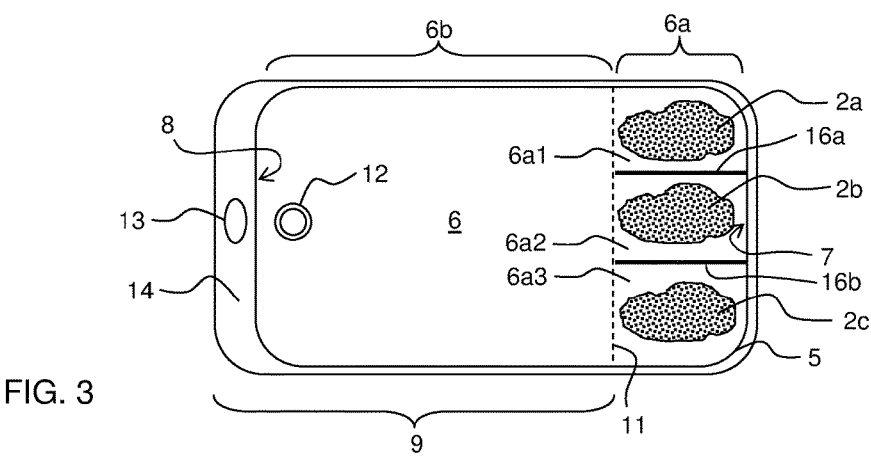
FIG. 3 is a top plan view of a unfolded package according to a third embodiment.

FIG. 3 is a top plan view of a third embodiment, which also contains three powder groups 2*a*, 2*b*, 2*c*. The third embodiment is only shown in the flat state, but it is realized that the resulting roll-up package 1 will be similar to the package shown in FIGS. 1C-1D. Like in the second embodiment, the powder groups 2*a*, 2*b*, 2*c* are located in a respective sub-cavity or pocket 6*a*1, 6*a*2, 6*a*3, but the sub-cavities 6*a*1, 6*a*2, 6*a*3 are arranged side by side in the axial direction of the roll-up package in the powder portion 6*a*. The sub-cavities 6*a*1, 6*a*2, 6*a*3 are separated by a respective elongated permanent partition 16*a*, 16*b* that connects the opposing sheets 3, 4. The respective partition 16*a*, 16*b* may be implemented by a weld line, glue or any alternative or equivalent permanent fixation means. The partitions 16*a*, 16*b* extend at right angles to the axial direction and to the border 11, which physically separates the sub-cavities 6*a*1, 6*a*2, 6*a*3 from the empty portion 6*b* in the roll-up package. The border 11 may be defined as in the first embodiment or any of its variants such that the powder groups 2*a*, 2*b*, 2*c* can enter the empty portion 6*b* and mix with the solvent during the preparation process, i.e. when the package is unfolded to the flat state.

Depending on implementation, the elongated partitions 16*a*, 16*b* need not be perpendicular to the axial direction of the package. Further, the elongated partitions 16*a*, 16*b* may be spaced from the first cavity end 7, especially if the partitions 16*a*, 16*b* are combined with other means for immobilizing the powder groups 2*a*, 2*b*, 2*c* in the respective sub-cavity 6*a*1, 6*a*2, 6*a*3, e.g. by evacuation of the cavity 6. It is also realized that it may be advantageous to replace the suspension hole 13 by a corresponding suspension hole in a frame portion at the first end 7, such that the powder groups 2*a*-2*c* fall into the empty portion 6*a* when the package is unfolded and suspended.

Figure 4:
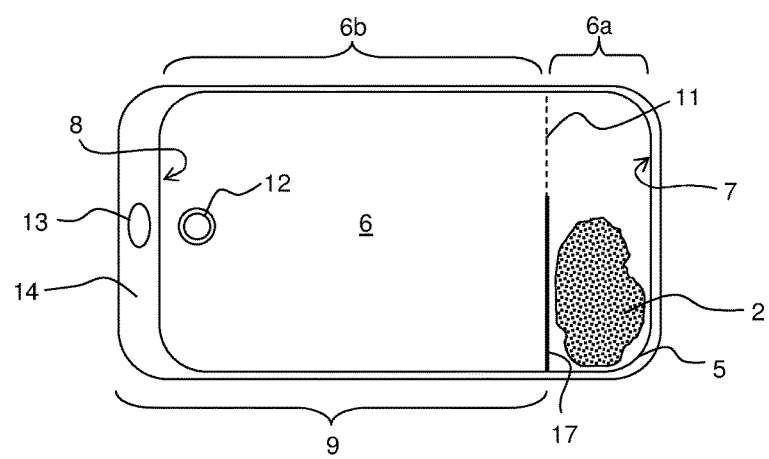
FIG. 4 is a top plan view of a unfolded package according to a fourth embodiment.

FIG. 4 is a top plan view of a fourth embodiment, which contains a single powder 2. The fourth embodiment is only shown in the flat state, but it is realized that the resulting roll-up package 1 will be similar to the package in FIGS. 1C-1D. The fourth embodiment differs from the first embodiment in that an elongated permanent partition 17 is arranged to extend along a part of the border 11 between the cavity portions 6*a*, 6*b*, so as to define a pocket for the powder 2. The pocket is located at one axial end of the package (cf. 104, 105 in FIG. 1D) and is open towards the other axial end in the powder portion 6*a*. The rest of the border 11, indicated by a dashed line, may be defined as in the first embodiment or any of its variants such that powder groups 2*a*-2*c* can enter the empty portion 6*a* when the package is unfolded.

Figure 5:
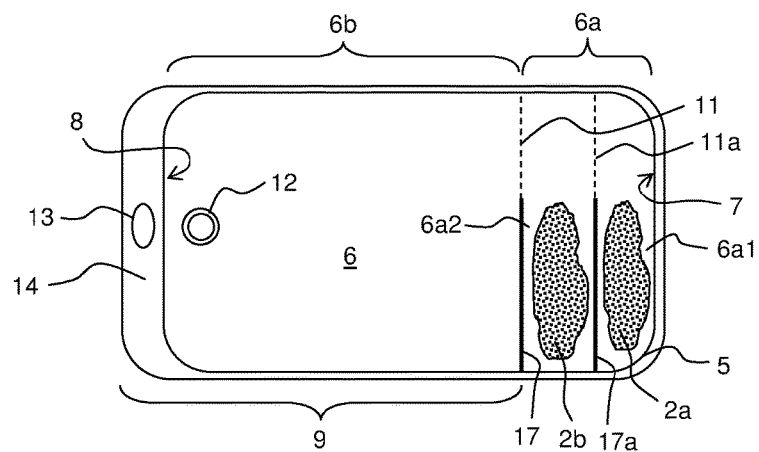
FIG. 5 is a top plan view of a variant of the unfolded package in FIG. 4.

FIG. 5 shows an implementation of the fourth embodiment for holding two powder groups 2*a*, 2*b* in the powder portion 6*a*. Each powder group 2*a*, 2*b* is located in a respective sub-cavity or pocket 6*a*1, 6*a*2. The sub-cavities 6*a*1, 6*a*2 are arranged side by side in the powder portion 6*a* to extend in the axial direction of the roll-up package. The sub-cavities 6*a*1, 6*a*2 are separated by a permanent partition 17*a* that extends in the axial direction of the package from one axial end about halfway to the other axial end. Like in FIG. 4, the cavity portions 6*a*, 6*b* are separated by a permanent partition 17 that also extends about halfway between the axial ends. Thereby, each sub-cavity 6*a*1, 6*a*2 is located at one axial end and is open towards the other axial end. Although not shown in the drawings, the sub-cavities 6*a*1, 6*a*2 may be folded one onto the other along the respective partition 17*a*, 17 starting from the innermost sub-cavity 6*a*1, similar to the embodiment in FIG. 2B. The folding may define a constriction region 11*a*.

Depending on implementation, the partitions 17, 17*a* need not be parallel to the axial direction of the package but may be angled towards the empty portion 6*a* to facilitate the transport of powder from the sub-cavities 6*a*1, 6*a*2 into the empty portion 6*b* when the package is unfolded. Further, the partitions 17, 17*a* may be spaced from both axial ends of the package.

Figure 6A:
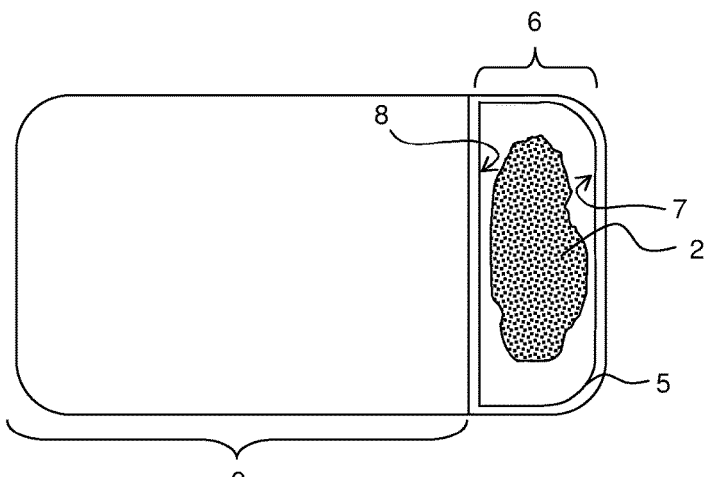
FIGS. 6A-6B are top plan and side views of an unfolded package according to a fifth embodiment
Figure 6B:
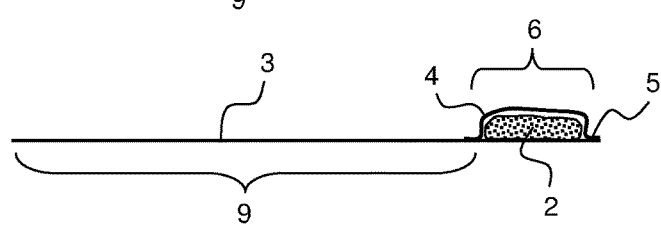

FIGS. 6A-6B show a fifth embodiment of the inventive package in a flat state, where the resulting roll-up package 1 is similar in shape to the package in FIGS. 1C-1D. In the fifth embodiment, the entire cavity 6 is used for storing the powder 2, and there is no empty cavity portion. A circumferential seal 5 joins the overlapping sheets 3, 4 to define the cavity 6, and the sheet 3 extends from the cavity 6 to form a tab 9. In a variant, the tab 9 is provided as a separate sheet (or plural overlapping sheets) which is attached, e.g. by welding, glue or the like, to a container that defines the cavity 6 and contains the powder 2. The container may have any configuration, e.g. it may be a flexible bag defined between overlapping sheets or it may be a more rigid structure. In one example, the container is formed as a tray of rigid material with a peelable lid. Irrespective of implementation, the tab is integrally formed with the cavity 6 that holds the powder 2 and is swept around the cavity 6 to form a roll-up package. It is understood that the cavity 6 may be designed to contain two or more powder groups, which are physically separated from each other, e.g. by constriction regions, fold lines, permanent partitions or releasable seals, or any combination thereof.

The package of the fifth embodiment has no internal space for mixing the powder with a solvent. Instead, the roll-up package is unfolded, the cavity is opened and the powder is emptied into separate mixing vessel, in which the powder is mixed with the solvent to form the dialysis solution.

Figure 7:
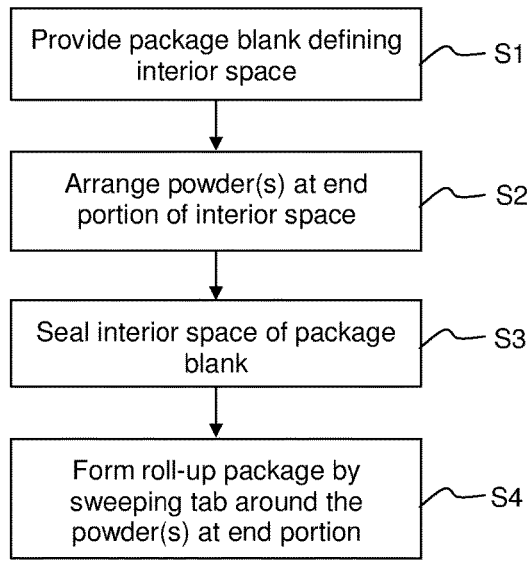
FIG. 7 is a flow chart of a generalized method for manufacturing a roll-up package.

FIG. 7 is a schematic overview of a process for manufacturing the roll-up package according to any of the above-described embodiments. The process includes steps S1-S4, which may be performed at a sequence of stations along a production line. In step S1, a package blank is provided to one of the stations. The package blank is a semi-finished product, i.e. an intermediate product, which is produced to define an interior space that will be sealed to form the cavity 6 in the end product. At this stage, the interior space is not yet sealed. The package blank as supplied in step S1 may, but need not, have the above-mentioned permanent partition(s), releasable seal(s), connector, suspension hole, etc. In step S2, the powder is dispensed, optionally in the form of powder groups, at one or more desired locations in the interior space, typically at the end that will form the first cavity end 7. In step S3, the interior space is sealed to form the interior cavity 6. Step S3 may also involve steps for providing fold line(s), permanent partition(s), releasable seal(s), connector, suspension hole, etc. Step S3 may also involve evacuating the interior cavity 6 to a sub-atmospheric pressure. Further, if the tab 9 is not already integrated in the package blank, a separate tab 9 is supplied and attached to the package blank in step S3. In step S4, the roll-up package is formed by sweeping the tab 9 around the powder(s) in the interior cavity 6. Step S4 may also involve folding sub-cavities in sequence as shown in FIG. 2B. A tape 10 may be attached to the roll-up package 1 to affix the tab 9.

While the disclosure has been described in connection with what is presently considered to be the most practical and preferred embodiments, it is to be understood that the disclosure is not to be limited to the disclosed embodiments, but on the contrary, is intended to cover various modifications and equivalent arrangements included within the spirit and the scope of the appended claims.

For example, the cavity 6 need have a rectangular perimeter as shown in the drawings, but may have another shape, such as circular, elliptical, rhombic, etc., for example to improve the mixing between the powder and the solvent. Likewise, the shape of the tab 9 may deviate from the rectangular shape shown in the drawings, for example to economize with sheet material or to facilitate the wrapping or unwrapping of the tab 9.

The invention claimed is:

1. A package for storing powdery material which is to be mixed with a solvent to form a medical solution, said package comprising:
    a filled cavity portion containing the powdery material, and
    a tab portion integrally formed with the filled cavity portion and being swept around the filled cavity portion so as to define a roll-up package, the tab portion including an empty cavity portion configured to receive the powdery material from the filled cavity portion when the roll-up package is unrolled, wherein the tab portion being swept around the filled cavity portion generates a force sufficient to maintain the powdery material in the filled cavity portion, and wherein the tab portion being unrolled from the filled cavity portion releases the force such that communication between the filled cavity portion and the empty cavity portion may be established.

2. The package of claim 1, wherein the roll-up package is generally cylindrical.

3. The package of claim 1, wherein the tab portion is swept in at least one full turn around the filled cavity portion.

4. The package of claim 1, which defines a sealed cavity that includes the filled cavity portion, and wherein the empty cavity portion is free of powdery material and is located adjacent to the filled cavity portion.

5. The package of claim 4, wherein the sealed cavity is evacuated to a sub-atmospheric pressure.

6. The package of claim 4, further comprising a connector attached to a wall portion of the empty cavity portion for admitting the solvent and enabling mixing of the powdery material with the solvent within the sealed cavity to form the medical solution.

7. The package of claim 4, comprising first and second overlapping sheets of flexible material which are joined to define the sealed cavity.

8. The package of claim 7, wherein the sealed cavity extends from a first cavity end to a second cavity end, the powdery material being arranged in the sealed cavity such that the filled cavity portion is located at the first cavity end and the empty cavity portion extends from the filled cavity portion towards the second cavity end.

9. The package of claim 8, wherein the filled cavity portion comprises a permanent partition which joins the first and second overlapping sheets and is arranged to at least partly locate the powdery material within the filled cavity portion.

10. The package of claim 9, wherein the permanent partition is arranged to extend in a direction from the first cavity end towards the second cavity end so that the filled cavity portion defines two pockets, and wherein a respective set of powdery material is arranged in the two pockets.

11. The package of claim 9, wherein the permanent partition is arranged with a spacing from the first cavity end such that an open pocket is defined between the permanent partition and the first cavity end in the filled cavity portion, and wherein at least part of the powdery material is contained in the open pocket.

12. The package of claim 8, wherein a plurality of sets of powdery material are located in the filled cavity portion side by side from the first cavity end towards the second cavity end, wherein at least two of the sets of powdery material have different hygroscopic properties, and wherein the set of powdery material that is most hygroscopic is located closest to the first cavity end.

13. The package of claim 7, wherein the filled cavity portion and the empty cavity portion are separated by a releasable seal that joins the first and second overlapping sheets.

14. The package of claim 7, wherein the filled cavity portion and the empty cavity portion are separated by a constriction region, in which the first and second overlapping sheets are brought into close proximity with each other without being fixedly attached to each other.

15. The package of claim 14, wherein the first and second overlapping sheets are brought into close proximity with each other in the constriction region at least partly by action of a force generated by the tab portion being swept around the filled cavity portion.

16. The package of claim 1, wherein the filled cavity portion contains at least two sets of powdery material of different compositions and is configured to physically separate the at least two sets of powdery material in the roll-up package.

17. The package of claim 1, wherein the medical solution is one of a dialysis concentrate, a dialysis solution, an infusion solution, a nutrition solution, a replacement solution, and a plasma expander solution.

18. The package of claim 1, wherein the powdery material comprises an acid concentrate powder for preparation of an acid concentrate for use in dialysis.

19. The package of claim 1, which is configured for use in a blood dialysis treatment or a peritoneal dialysis treatment.

20. A package for storing powdery material which is to be mixed with a solvent to form a medical solution, said package comprising:
    a filled cavity portion containing the powdery material,
    a tab portion connected to the filled cavity portion, the tab portion sized to wrap around the filled cavity portion at least one time and including an empty cavity portion configured to receive the powdery material from the filled cavity portion when the tab portion is unwrapped from the filled cavity portion, wherein the tab portion being swept around the filled cavity portion generates a force sufficient to maintain the powdery material in the filled cavity portion, and wherein the tab portion being unrolled from the filled cavity portion releases the force such that communication between the filled cavity portion and the empty cavity portion may be established; and
    a connector attached to the tab portion for admitting the solvent to enable mixing of the powdery material with the solvent to form the medical solution.

* * * * *